(12) United States Patent
Blaine et al.

(10) Patent No.: US 10,166,260 B2
(45) Date of Patent: Jan. 1, 2019

(54) WOUND CARE PRODUCT WITH EGG SHELL MEMBRANE

(71) Applicants: Robert C. Blaine, Buena Park, CA (US); Thang D. Ngo, Garden Grove, CA (US)

(72) Inventors: Robert C. Blaine, Buena Park, CA (US); Thang D. Ngo, Garden Grove, CA (US)

(73) Assignee: Blaine Laboratories, Inc., Santa Fe Springs, CA (US)

( * ) Notice: Subject to any disclaimer, the term of this patent is extended or adjusted under 35 U.S.C. 154(b) by 150 days.

(21) Appl. No.: 13/901,697

(22) Filed: May 24, 2013

(65) Prior Publication Data

US 2014/0348939 A1 Nov. 27, 2014

(51) Int. Cl.
*A61K 35/56* (2015.01)
*A61K 31/14* (2006.01)
*A61K 31/728* (2006.01)
*A61K 35/57* (2015.01)

(52) U.S. Cl.
CPC ............. *A61K 35/56* (2013.01); *A61K 31/14* (2013.01); *A61K 31/728* (2013.01); *A61K 35/57* (2013.01)

(58) Field of Classification Search
None
See application file for complete search history.

(56) References Cited

U.S. PATENT DOCUMENTS

| | | | |
|---|---|---|---|
| 1,251,720 A | 1/1918 | Wege | |
| 3,194,732 A | 7/1965 | Neuhauser | |
| 3,196,075 A * | 7/1965 | Neuhauser | 602/48 |
| 6,541,447 B1 * | 4/2003 | Dawson | 514/9.1 |
| 6,946,551 B2 * | 9/2005 | Long | A61K 8/982 |
| | | | 536/55.1 |
| 7,041,868 B2 | 5/2006 | Greene et al. | |
| 8,425,943 B2 | 4/2013 | Strohbehn et al. | |
| 2004/0180025 A1 * | 9/2004 | Long et al. | 424/70.14 |
| 2005/0107302 A1 | 5/2005 | Dawson | |
| 2007/0178170 A1 | 8/2007 | DeVore et al. | |
| 2009/0074879 A1 | 3/2009 | Braguti et al. | |

FOREIGN PATENT DOCUMENTS

| | | | | |
|---|---|---|---|---|
| EP | 2774655 A1 * | 9/2014 | | A61K 8/73 |
| GB | 1251720 | 10/1971 | | |
| JP | 52012514 A * | 1/1977 | | |
| JP | 77012514 B * | 4/1977 | | |
| JP | 77012514 B * | 4/1977 | | |
| JP | 2002265311 A | 9/2002 | | |
| JP | 2003081728 A | 3/2003 | | |
| JP | 2003225298 A * | 8/2003 | | |
| JP | 3615860 B2 | 2/2005 | | |
| JP | 2006158354 A * | 6/2006 | | |
| JP | 3897600 B2 | 3/2007 | | |
| JP | 2007070246 A | 3/2007 | | |
| JP | 2007197393 A * | 8/2007 | | |
| JP | 2008007419 A * | 1/2008 | | |
| WO | 2005107774 | 11/2005 | | |
| WO | WO 2010122490 A2 * | 10/2010 | | |
| WO | WO2010122490 A2 * | 10/2010 | | |
| WO | 2012036645 | 3/2012 | | |
| WO | WO 2012/036645 A2 | 3/2012 | | |

OTHER PUBLICATIONS

BIOVA, http://www.biova.com/index.php?option=com_content&view=article&id=6&Itemid=6 [retrieved from the internet Jul. 24, 2013], 1 page.
JP3615860, Asahi Optical—English Abstract.
JP3897600, NOEVIR—English Abstract.
JP2007070246, ALMADO—English Abstract.
Eri, Ohto-Fujita et al., "Hydrolized eggshell membrane immobilized on phosphorylcholilne polymer supplies extracellular matrix environment for human derman fibroblasts", Cell and Tissue Research, May 20, 2011, vol. 345, Issue 1, pp. 177-190.
PCT/US2014/039271 Blaine Laboratories, Inc., "Notification of Transmittal of The International Search Report and The Written Opinion of the International Searching Authority, or The Declaration", dated Sep. 12, 2014.

* cited by examiner

*Primary Examiner* — Amy L Clark
(74) *Attorney, Agent, or Firm* — McKee, Voorhees & Sease, PLC

(57) ABSTRACT

A wound care product in the form of a gel is provided, and contains protein from egg shell membrane. The gel is made by first hydrating the egg shell membrane powder and then adding carbomer to partially neutralize the egg shell membrane. The neutralization is completed with the addition of triethanolamine, so as to form a homogeneous gel with a smooth consistency. An antimicrobial compound and a tissue growth accelerator are added to the gel. The gel, infused with egg shell membrane, is applied directly to the wound tissue to form a barrier trapping the active ingredients adjacent the wound site and inhibiting penetration of outside bacteria into the wound site.

12 Claims, 1 Drawing Sheet

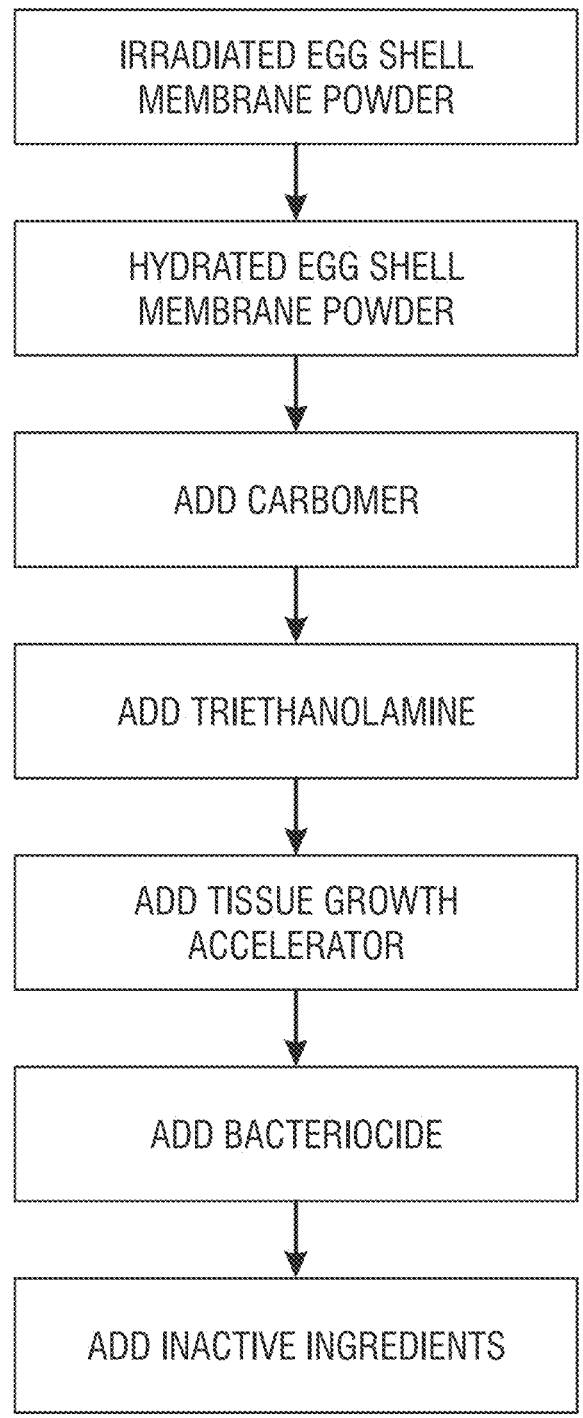

WOUND CARE PRODUCT WITH EGG SHELL MEMBRANE

FIELD OF THE INVENTION

The invention relates to wound care compositions and methods of use in treating wounds. In particular, the wound care compositions employ egg shell membrane.

BACKGROUND OF THE INVENTION

Many different types of products have been known for use in wound care and treatment. The prior art literature discusses the use egg shell membrane for treating wounds. See, for example, Neuhauser U.S. Pat. Nos. 3,194,732 and 3,196,075 and British Patent 1,251,720. However, egg shell membrane is rich in protein, which promotes bacteria growth. It is undesirable to use any product that promotes the growth of bacteria on an open wound.

A wound care product in the form of a gel is often desirable, since the gel forms a barrier to retain active ingredients in the wound sight and preclude migration of exterior bacteria into the wound sight. However, the addition of egg shell membrane in a powder form creates a lumpy, globular gel which is undesirable.

Therefore, the primary objective of the present invention is the provision of an improved wound care gel containing protein from egg shell membrane.

Another objective of the present invention is the provision of a homogenous gel having egg shell membrane therein for use in wound treatment and care.

A further objective of the present invention is the provision of a method of treating a wound using an egg shell membrane gel.

A further objective of the present invention is the provision of a method of making a smooth, homogenous gel having egg shell membrane for use in wound care.

Still another objective of the present invention is the provision of a wound care gel having irradiated egg shell membrane therein.

Still another objective of the present invention is the provision of a wound care gel having egg shell membrane, a tissue growth accelerator, and an antimicrobial compound.

A further objective of the present invention is the provision of a wound care gel having protein from egg shell membrane, which is economical to manufacture and effective in use.

These and other objectives will become apparent from the following description of the invention.

SUMMARY OF THE INVENTION

The wound care product of the present invention is a gel containing egg shell membrane, an antimicrobial compound, and a tissue growth accelerator. The wound care product is made by first hydrating egg shell membrane powder. A carbomer is then added to the hydrated egg shell membrane so as to partially neutralize the membrane. Then, a different neutralizing agent is added to the carbomer and egg shell member so as to complete neutralization of the membrane, and thereby form a consistably smooth and homogenous gel for treating wounds. An antibiotic and a tissue growth accelerator are added to the gel before use.

In use, the egg shell membrane gel is applied to the wound site so as to coat the wound tissue. As the gel dries, a protective barrier is formed over the wound tissue to retain active ingredients in contact with the tissue and to prohibit migration of exterior bacteria into the wound site.

Various inactive ingredients can be added to the egg shell membrane gel so as to create a satisfactory shelf life.

BRIEF DESCRIPTION OF THE DRAWINGS

FIG. 1 is a flow diagram of the method of making the wound care product of the present invention.

DETAILED DESCRIPTION OF THE INVENTION

All units, prefixes, and symbols may be denoted in its SI accepted form. Numeric ranges recited within the specification are inclusive of the numbers defining the range and include each integer within the defined range (e.g., 1 to 5 includes 1, 1.5, 2, 2.75, 3, 3.80, 4, and 5).

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities. Moreover, whether or not values in the specification, including numerical ranges in tables, are modified by the term "about", the term "about" should be understood to apply to those values unless otherwise specified.

The term "antimicrobial" means compositions that can affect two kinds of microbial cell damage. The first is a lethal, irreversible action resulting in complete microbial cell destruction or incapacitation and termed microbiocidal. The second type of cell damage is reversible, such that if the organism is rendered free of the agent, it can again multiply and termed microbistatic. Antimicrobials of the present invention may affect microbiocidal activity, microbistatic activity, or a combination of both.

The wound care gel composition of the present invention is intended for external use in treating tissue wounds to promote healing and prevent infection. For example, this wound care product can be used for lacerations, skin tears, abrasions, surgical incisions sites, device insertion sites, stasis ulcers, pressure ulcers, diabetic ulcers, first and second degree burns, graft sites, and donor sites. Preferably, the gel is applied to the wound site about ⅛" to about ¼" thick, and then covered with appropriate dressing. As the gel dries, a barrier is formed to retain the active ingredients adjacent the tissue to enhance healing of the tissue, while precluding penetration of bacteria.

The wound care product contains protein from irradiated egg shell membrane which is free from egg shells. The gel also contains an antimicrobial compound, such as benzalkonium chloride, as well as a tissue growth accelerator, such as hyaluronic acid. The egg shell membrane has tissue growth factors, including Transforming Growth Factor-b, collagen and elastin.

The egg shell membrane comprises about 0.1% to about 10%, and preferably from about 1.0% to about 8.0% by weight of active material relative to the total weight of the mixture.

The aqueous phase (deionized water) of the gel product can constitute, for example, from about 70.0% to about 99.9%, and preferable from about 80.0% to about 90.0% by weight relative to the total weight of the mixture.

The carbomer of the wound care product ranges, for example, from about 0.1% to about 5.0%, and preferably from about 0.5% to about 4.0% by weight of active material relative to the total weight of the mixture.

The wound care product also contains triethanolamine ranging, for example, from about 0.1% to about 5.0%, and preferably from about 0.5% to about 4.0% by weight active material relative to the total weight of the mixture.

The wound care gel also contains glycerine ranging, for example, from about 0.5% to about 10.0%, and preferably from about 1.0% to about 7.0% by weight of active material relative to the total weight of the mixture.

The wound care composition includes an antimicrobial compound. Suitable antimicrobial compounds include, but are not limited to, quaternary ammonium compounds such as benzalkonium chloride. The antimicrobial compound may be from about 0.001% to about 0.10%, and preferably from about 0.05% to about 0.10% by weight of active material relative to the total weight of the mixture. In a particular embodiment of the invention, benzalkonium chloride is provided in the wound care gel ranging, for example, from about 0.001% to about 0.10%, and preferably from about 0.05% to about 0.10% by weight of active material relative to the total weight of the mixture.

The wound care product also contains an amount of hyaluronic acid ranging, for example, from about 0.0001% to about 1.0%, and preferable from about 0.001% to about 0.10% by weight of active material relative to the total weight of the mixture.

The wound care gel product also contains inactive ingredients, preferably not greater than about 5%, and more preferably not greater than about 1.0%, and most preferably not greater than about 0.5% by weight, of water compatible substances.

The following table summarizes one embodiment of the wound care gel product according to the present invention.

WOUND CARE GEL

| Ingredient | Range % by weight | Preferred range |
| --- | --- | --- |
| Egg Shell Membrane | 0.1-10 | 1.0-8.0 |
| Deionized Water | 70-99.9 | 80-90 |
| Carbomer | 0.1-5.0 | 0.5-4.0 |
| Triethanolamine | 0.1-5.0 | 0.5-4.0 |
| Glycerine | 0.5-10.0 | 1.0-7.0 |
| Benzalkonium Chloride | 0.001-0.10 | 0.05-0.10 |
| Hyaluronic Acid | 0.0001-1.0 | 0.001-0.10 |
| Inactive Ingredients | 0-5.0 | 0-1.0 |

The wound care composition also includes numerous inactive ingredients. For example, the inactive ingredients may include aloe vera leaf juice and oil extract, phenoxyethanol, methylparaben, ethylparaben, propylparaben, butylparaben, and isobutylparaben. Such inactive ingredients may be present from about 0% to about 5.0%, or from about 0% to about 1.0% by weight of the wound care composition.

The wound care gel product containing the complex protein from egg shell membranes is prepared in the following manner. Before preparing the gel, the egg shell membrane, typically in the form of a powder, is subjected to radiation to kill all bacteria. The irradiated powdered egg shell membrane, is mixed with an aqueous phase, such as deionized water, until completely dissolved. This forms a yellow aqueous protein solution which is slightly hazy. Any known method of mixing may be used. Preferably, both sweep and helical agitation is used in mixing the egg protein at a rate of 50-1000 rpm for up to approximately two hours. However, in particular embodiments either sweep or helical agitation may be used.

In the next step of the process, carbomer is added to the protein solution and is mixed to form a thick, globular gel in the mixing container. Again, preferably this mixing step is achieved with both sweep and helical agitation at a rate 50-1000 rpm for up to two hours. This step partially neutralizes the protein.

In the next step, glycerine is added to the stiff gel and mixed, preferably with both sweep and helical agitation at a rate of 50-1000 rpm for up to two hours, although in particular embodiments sweep agitation, helical agitation, or any other known method of mixing may be used.

Next, triethanolamine is added to the gel and mixed so as to form a smooth, fully neutralized gel, preferably using both sweep and helical agitation at a rate of 50-1200 rpm for up to two hours, although in particular embodiments sweep agitation, helical agitation, or any other known method of mixing may be used. Then, benzalkonium chloride is added and mixed until uniform, preferably using both sweep and helical agitation at a rate of 50-500 rpm for up to two hours. Next, hyaluronic acid is added and mixed into the gel, preferably with sweep and helical agitation at a rate of 50-500 rpm for up to two hours, although in particular embodiments sweep agitation, helical agitation, or any other known method of mixing may be used. Lastly, the inactive ingredients are added to the mixture until the gel is smooth and uniform.

The wound compound preparation process is unique due to the utilization of the amphoteric properties of the complex egg shell membrane proteins.

CLINICAL STUDY EXAMPLE

Preliminary results from a 54 patient clinical pilot study prove promising results regarding the efficacy of a wound care gel containing benzalkonium chloride (0.01 wt. %) with gamma irradiated chicken egg membrane protein (5 wt. %) on open chronic Diabetic lower extremity wounds. All wounds had been treated with topical antibiotic products and all patients were on systemic antibiosis. At the beginning of the study none of the wound cultures demonstrated active infection.

51 patients with 54 lower extremity diabetic wounds from three unrelated foot and ankle diabetic clinics represented the population studied. Each wound was present an average of 4-5 months (1 month to 11 months), initially averaging 1.50 cm (1.01 cm -4.01 cm)×1.01 cm (0.60 cm-1.42 cm)× 0.23 cm (0.10 cm-1.70 cm), and all wounds had been treated at least 4-6 weeks with 2-3 different wound care products (Silvadene, Granulex and Santyl) that had failed to effect the quality, size and depth of the wounds. Patients were instructed as to the daily use of the proprietary wound care gel and given wound care packets for daily dressing changes. Any oral antibiotics the patients were receiving were maintained. The wounds were evaluated weekly in the three different clinics by two podiatric surgical residents and covariate analysis compared reduction in wound area (size and depth) from initial wound baseline measurements.

After one week of once-daily application of the product by the patient, 41 wounds (75%) demonstrated visible increased beefy red granulation, 13 wounds (25%) reduced in size by >50%, 33 wounds (62%) reduced in size by >10% <50%, and 8 wounds (13%) did not change size. Of the wounds that remained unchanged, 5 demonstrated osteomyelitis at the wound site.

After 3 weeks of daily use of the proprietary wound care gel, 26 wounds (49%) had reduced in size by >50%, 23 wounds (43%) reduced in size by >10% <50%, 5 wounds (9%) did not change in size. No patients reported any adverse effects.

This study provides preliminary results suggesting that this proprietary wound care product is safe and clearly effective in accelerating the healing of diabetic lower extremity wounds that did not respond to at least two different previous topical treatments. The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A wound care gel, comprising:
    a) irradiated egg shell membrane comprising protein, wherein said irradiated egg shell membrane is present in an amount of about 0.1 to about 10% by weight;
    b) an antimicrobial compound in an amount of about 0.001 to about 0.1% by weight;
    c) an effective amount of a tissue growth accelerator; and optionally
    d) inactive ingredients;
    wherein said wound care gel is obtained by:
       i. mixing the irradiated eggshell membrane with an aqueous phase to provide a protein solution;
       ii. partially neutralizing the protein solution by adding carbomer to provide a partially neutralized protein gel;
       iii. optionally adding glycerin to the partially neutralized protein gel;
       iv. adding triethanolamine to the partially neutralized protein gel of step ii) or step iii) to provide a neutralized gel;
       v. adding the antimicrobial compound to the neutralized gel;
       vi. adding the tissue growth accelerator; and optionally
       vii. adding inactive ingredients.

2. The wound care gel of claim 1, wherein the tissue growth accelerator is hyaluronic acid.

3. The wound care gel of claim 1, wherein the antimicrobial compound is a quaternary ammonium compound.

4. The wound care gel of claim 3, wherein the antimicrobial compound comprises benzalkonium chloride and is approximately 0.5% -0.1% by weight of the gel.

5. The wound care gel of claim 1, wherein the protein in egg shell membrane is neutralized in a two-step process.

6. The wound care gel of claim 1, wherein the gel is free from egg shell.

7. A wound care gel, consisting essentially of:
    a) irradiated egg shell membrane comprising protein, wherein said irradiated egg shell membrane is present in an amount of about 0.1 to about 10% by weight;
    b) an antimicrobial compound in an amount of about 0.001 to about 0.1% by weight;
    c) an effective amount of hyaluronic acid; and optionally
    d) inactive ingredients;
    wherein said wound care gel is obtained by:
       i. mixing the irradiated eggshell membrane with an aqueous phase to provide a protein solution;
       ii. partially neutralizing the protein solution by adding carbomer to provide a partially neutralized protein gel;
       iii. optionally adding glycerin to the partially neutralized protein gel;
       iv. adding triethanolamine to the partially neutralized protein gel of step ii) or step iii) to provide a neutralized gel;
       v. adding the antimicrobial compound to the neutralized gel;
       vi. adding the tissue growth accelerator; and optionally
       vii. adding inactive ingredients.

8. The wound care gel of claim 7, wherein the antimicrobial compound is benzalkonium chloride.

9. The wound care gel of claim 7, wherein the egg shell membrane is about 1% to about 8% by weight.

10. A method of treating a wound, comprising:
    applying the wound care gel of claim 1 to the wound; and
    allowing the gel to dry, wherein the gel forms a barrier over the wound and inhibits penetration of bacteria through the barrier.

11. The method of claim 10, wherein the egg shell membrane is free from egg shell.

12. The method of claim 10, wherein the gel contains hyaluronic acid as an added ingredient apart from the egg shell membrane.

* * * * *